US012344634B2

(12) United States Patent
Tucker et al.

(10) Patent No.: US 12,344,634 B2
(45) Date of Patent: *Jul. 1, 2025

(54) PEPTIDES FOR CHARACTERIZATION OF *botulinum* NEUROTOXINS

(71) Applicant: BIOMADISON, INC, Del Mar, CA (US)

(72) Inventors: Ward C. Tucker, Monona, WI (US); Francis Mark Dunning, Madison, WI (US)

(73) Assignee: BioMadison, Inc., Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/747,818

(22) Filed: Jun. 19, 2024

(65) Prior Publication Data

US 2025/0002537 A1    Jan. 2, 2025

Related U.S. Application Data

(63) Continuation of application No. 18/137,604, filed on Apr. 21, 2023, now Pat. No. 12,054,516, which is a continuation of application No. 17/208,649, filed on Mar. 22, 2021, now Pat. No. 11,661,442, which is a continuation of application No. 16/712,462, filed on Dec. 12, 2019, now Pat. No. 10,975,125, which is a continuation of application No. 16/267,155, filed on Feb. 4, 2019, now Pat. No. 10,508,135, which is a continuation of application No. 14/941,452, filed on Nov. 13, 2015, now Pat. No. 10,246,492, which is a continuation-in-part of application No. 13/502,357, filed as application No. PCT/US2010/052847 on Oct. 15, 2010, now Pat. No. 9,453,254.

(60) Provisional application No. 61/252,315, filed on Oct. 16, 2009.

(51) Int. Cl.
| | |
|---|---|
| C07K 14/00 | (2006.01) |
| C12N 9/52 | (2006.01) |
| C12Q 1/37 | (2006.01) |
| G01N 33/542 | (2006.01) |

(52) U.S. Cl.
CPC ............... *C07K 14/00* (2013.01); *C12N 9/52* (2013.01); *C12Q 1/37* (2013.01); *G01N 33/542* (2013.01); *G01N 2333/33* (2013.01)

(58) Field of Classification Search
CPC . C07K 14/00; C12N 9/52; C12Q 1/37; G01N 33/542; G01N 2333/33
See application file for complete search history.

(56) References Cited

U.S. PATENT DOCUMENTS

2006/0134722 A1* 6/2006 Chapman ............ C07K 14/435
                                                    435/23
2012/0322092 A1* 12/2012 Tucker ..................... C12Q 1/37
                                                    435/23

* cited by examiner

*Primary Examiner* — Paul J Holland
(74) *Attorney, Agent, or Firm* — Fish IP Law, LLP (57) ABSTRACT

Recombinant nucleic acids encoding reporting constructs for characterizing *botulinum* neurotoxin protease activity and cells that incorporate such recombinant nucleic acids and that are suitable for use in cell-based assays for the neurotoxin are provided. The encoded reporting constructs are a pair of recombinant hybrid proteins that act in concert, and can include an N-terminal palmitoylation sequence. The reporting constructs are a pair of recombinant hybrid proteins that act in concert, and that include a *botulinum* neurotoxin protease recognition and cleavage sequence positioned to release a fluorophore upon cleavage.

9 Claims, 8 Drawing Sheets
Specification includes a Sequence Listing.

EXCITATION → CFP
FRET ↓
YFP ← BoNT/A

EXCITATION → CFP
EMISSION ↓
YFP

+BoNT/B →

LOSS OF
INTRAMOLECULAR
FRET

```
                            SEQUENCE LISTING

Sequence total quantity: 9
SEQ ID NO: 1            moltype = DNA  length = 1839
FEATURE                 Location/Qualifiers
misc_feature            1..1839
                        note = Recombinant coding sequence for pMD0031
misc_feature            1..717
                        note = Enhanced Cyan Fluorescent Protein
misc_feature            718..753
                        note = Linker
misc_feature            754..1017
                        note = N-terminal portion of VAMP2 including all cleavage
                         sites and no transmembrane domain
misc_feature            1018..1026
                        note = SGG Linker
misc_feature            1027..1743
                        note = Yellow Fluorescent Protein
misc_feature            1744..1752
                        note = SGG Linker
misc_feature            1753..1839
                        note = C-terminal portion of VAMP2 including transmembrane
                         domain and no cleavage sites
source                  1..1839
                        mol_type = other DNA
                        organism = synthetic construct
SEQUENCE: 1
atggtgagca agggcgagga gctgttcacc ggggtggtgc ccatcctggt cgagctggac  60
ggcgacgtaa acggccacaa gttcagcgtg tccggcgagg gcgagggcga tgccacctac 120
ggcaagctga cctgaagtt catctgcacc accggcaagc tgcccgtgcc ctggcccacc 180
ctcgtgacca cctgacctg gggcgtgcag tgcttcagc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacat cagccacaac gtctatatca ccgccgacaa gcagaagaac 480
ggcatcaagg ccaacttcaa gatccgccac aacatcgagg acggcagcgt gcagctgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtcc 720
ggactcagat ctcgactca agcttcgaat tctatgtcgg ctaccgctgc caccgtcccg 780
cctgccgccc cggccggcga gggtggcccc cctgcacctg ctccaaatct taccagtaac 840
aggagactgc agcagaccca ggcccaggtg gatgaggtgg tggacatcat gagggtgaat 900
gtggacaagg tcctggagcg ggaccagaag ctatcggaac tggatgatcg cgcagatgcc 960
ctccaggcag gggcctccca gtttgaaaca agtgcagcca agctcaagcg caaatactcg 1020
ggaggcatgg tgagcaaggg cgaggagctg ttcaccgggg tggtgcccat cctggtcgag 1080
ctgacggcg acgtaaacgg ccacaagttc agcgtgtccg gcgagggcga gggcgatgcc 1140
acctacggca agctgaccct gaagttcatc tgcaccaccg gcaagctgcc cgtgccctgg 1200
cccaccctcg tgaccacctt cggctacggc ctgcagtgct tcgcccgcta ccccgaccac 1260
atgaagcagc acgacttctt caagtccgcc atgcccgagg gctacgtcca ggagcgcacc 1320
atcttcttca aggacgacgg caactacaag acccgcgccg aggtgaagtt cgagggcgac 1380
accctggtga accgcatcga gctgaagggc atcgacttca aggaggacgg caacatcctg 1440
gggcacaagc tggagtacaa ctacaacagc cacaacgtct atatcatggc cgacaagcag 1500
aagaacggca tcaaggtgaa cttcaagatc cgccacaaca tcgaggacgg cagcgtgcag 1560
ctcgccgacc actaccagca gaacacccccc atcggcgacg gccccgtgct gctgcccgac 1620
```

```
aaccactacc tgagctacca gtccgccctg agcaaagacc ccaacgagaa gcgcgatcac  1680
atggtcctgc tggagttcgt gaccgccgcc gggatcactc tcggcatgga cgagctgtac  1740
aagagcggcg gttggtggaa aaacctcaag atgatgatca tcttgggagt gatttgcgcc  1800
atcatcctca tcatcatcat cgtttacttc agcacttaa                         1839
```

```
SEQ ID NO: 2              moltype = AA   length = 612
FEATURE                   Location/Qualifiers
REGION                    1..612
                          note = Recombinant protein encoded by pMD0031
REGION                    1..239
                          note = MISC_FEATURE - Enhanced Cyan Fluorescent Protein
REGION                    240..251
                          note = MISC_FEATURE - Linker
REGION                    252..339
                          note = MISC_FEATURE - N-terminal portion of VAMP2 including
                           all cleavage sites and no transmembrane domain
REGION                    340..342
                          note = MISC_FEATURE - SGG Linker
REGION                    343..581
                          note = MISC_FEATURE - Yellow Fluorescent Protein
REGION                    582..584
                          note = MISC_FEATURE - SGG Linker
REGION                    585..612
                          note = MISC_FEATURE - C-terminal portion of VAMP2 including
                           transmembrane domain and no cleavage sites
source                    1..612
                          mol_type = protein
                          organism = synthetic construct
SEQUENCE: 2
MVSKGEELFT GVVPILVELD GDVNGHKFSV SGEGEGDATY GKLTLKFICT TGKLPVPWPT   60
LVTTLTWGVQ CFSRYPDHMK QHDFFKSAMP EGYVQERTIF FKDDGNYKTR AEVKFEGDTL  120
VNRIELKGID FKEDGNILGH KLEYNYISHN VYITADKQKN GIKANFKIRH NIEDGSVQLA  180
DHYQQNTPIG DGPVLLPDNH YLSTQSALSK DPNEKRDHMV LLEFVTAAGI TLGMDELYKS  240
GLRSRAQASN SMSATAATVP PAAPAGEGGP PAPPPNLTSN RRLQQTQAQV DEVVDIMRVN  300
VDKVLERDQK LSELDDRADA LQAGASQFET SAAKLKRKYS GGMVSKGEEL FTGVVPILVE  360
LDGDVNGHKF SVSGEGEGDA TYGKLTLKFI CTTGKLPVPW PTLVTTFGYG LQCFARYPDH  420
MKQHDFFKSA MPEGYVQERT IFFKDDGNYK TRAEVKFEGD TLVNRIELKG IDFKEDGNIL  480
GHKLEYNYNS HNVYIMADKQ KNGIKVNFKI RHNIEDGSVQ LADHYQQNTP IGDGPVLLPD  540
NHYLSYQSAL SKDPNEKRDH MVLLEFVTAA GITLGMDELY KSGGWWKNLK MMIILGVICA  600
IILIIIIVYF ST                                                     612
```

```
SEQ ID NO: 3              moltype = DNA   length = 1077
FEATURE                   Location/Qualifiers
misc_feature              1..1077
                          note = Recombinant coding sequence for intermolecular
                           construct with YFP
misc_feature              1..717
                          note = Yellow Fluorescence Protein
misc_feature              718..726
                          note = SGG Linker
misc_feature              727..1077
                          note = Full-length VAMP2 with transmembrane domain and
                           cleavage sites
source                    1..1077
                          mol_type = other DNA
                          organism = synthetic construct
SEQUENCE: 3
atggtgagca aggggcgagga gctgttcacc ggggtggtgc ccatcctggt cgagctggac   60
ggcgacgtaa acggccacaa gttcagcgtg tccggcgagg gcgagggcga tgccaccta   120
ggcaagctga ccctgaagtt catctgcacc accggcaagc tgcccgtgcc ctggcccacc   180
ctcgtgacca ccttcggcta cggcctgcag tgcttcgccc gctacccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gacccccaacg agaagcgcga tcacatggtc   660
ctgctgagct tcgtgaccgc cgccgggatc actctcggca tggacgagct gtacaagagt   720
ggaggcatgt cggctaccgc tgccaccgtc ccgcctgccg cccggcggg agagggtggc   780
cccctgcac ctcctccaaa tcttaccagt aacaggagac tgcagcagac ccaggccag   840
gtggatgagg tggtggacat catgagggtg aatgtggaca ggtcctgga gcagaccag   900
aagctatcgg aactggatga tcgcgcagat gccctccagg caggggcctc ccagtttgaa   960
acaagtgcag ccaagctcaa gcgcaaatac tggtggaaaa acctcaagat gatgatcatc  1020
ttgggagtga tttgcgccat catcctcatc atcatcatcg tttacttcag cacttaa    1077
```

```
SEQ ID NO: 4              moltype = AA   length = 358
FEATURE                   Location/Qualifiers
REGION                    1..358
```

```
                        note = Recombinant protein encoded by pMD0034 YFP
REGION                  1..239
                        note = MISC_FEATURE - Yellow Fluorescence Protein
REGION                  240..242
                        note = MISC_FEATURE - SGG Linker
REGION                  243..358
                        note = MISC_FEATURE - Full-length VAMP2 with transmembrane
                         domain and cleavage sites
source                  1..358
                        mol_type = protein
                        organism = synthetic construct
SEQUENCE: 4
MVSKGEELFT GVVPILVELD GDVNGHKFSV SGEGEGDATY GKLTLKFICT TGKLPVPWPT    60
LVTTFGYGLQ CFARYPDHMK QHDFFKSAMP EGYVQERTIF FKDDGNYKTR AEVKFEGDTL   120
VNRIELKGID FKEDGNILGH KLEYNYNSHN VYIMADKQKN GIKVNFKIRH NIEDGSVQLA   180
DHYQQNTPIG DGPVLLPDNH YLSYQSALSK DPNEKRDHMV LLEFVTAAGI TLGMDELYKS   240
GGMSATAATV PPAAPAGEGG PPAPPPNLTS NRRLQQTQAQ VDEVVDIMRV NVDKVLERDQ   300
KLSELDDRAD ALQAGASQFE TSAAKLKRKY WWKNLKMMII LGVICAIILI IIIVYFST    358

SEQ ID NO: 5            moltype = DNA  length = 1077
FEATURE                 Location/Qualifiers
misc_feature            1..1077
                        note = Recombinant coding sequence for intermolecular
                         construct with ECFP
misc_feature            1..717
                        note = Enhanced Cyan Fluorescence Protein
misc_feature            718..726
                        note = SGG Linker
misc_feature            727..1077
                        note = Full-length VAMP2 with transmembrane domain and
                         cleavage sites
source                  1..1077
                        mol_type = other DNA
                        organism = synthetic construct
SEQUENCE: 5
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgacctg gggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacat cagccacaac gtctatatca ccgccgacaa gcagaagaac   480
ggcatcaagg ccaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagagt   720
ggaggcatgt cggctaccgc tgccaccgtc ccgcctgccg cccgggcggg cgagggtggc   780
ccccctgcac ctcctccaaa tcttaccagt aacaggagac tgcagcagac ccaggcccag   840
gtggatgagg tggtggacat catgagggtg aatgtggaca aggtcctgga gcgagaccag   900
aagctcatcg aactggatga tcgcgcagat gccctccagg cgggcgcctc ccagtttgaa   960
acaagtgcag ccaagctcaa gcgcaaatac tggtggaaaa acctcaagat gatgatcatc   1020
ttgggagtga tttgcgccat catcctcatc atcatcatcg tttacttcag cacttaa    1077

SEQ ID NO: 6            moltype = AA  length = 358
FEATURE                 Location/Qualifiers
REGION                  1..358
                        note = Recombinant protein encoded by pMD0034 ECFP
REGION                  1..239
                        note = MISC_FEATURE - Enhanced Cyan Fluorescence Protein
REGION                  140..242
                        note = MISC_FEATURE - SGG Linker
REGION                  243..358
                        note = MISC_FEATURE - Full-length VAMP2 with transmembrane
                         domain and cleavage sites
source                  1..358
                        mol_type = protein
                        organism = synthetic construct
SEQUENCE: 6
MVSKGEELFT GVVPILVELD GDVNGHKFSV SGEGEGDATY GKLTLKFICT TGKLPVPWPT    60
LVTTLTWGVQ CFSRYPDHMK QHDFFKSAMP EGYVQERTIF FKDDGNYKTR AEVKFEGDTL   120
VNRIELKGID FKEDGNILGH KLEYNYISHN VYITADKQKN GIKANFKIRH NIEDGSVQLA   180
DHYQQNTPIG DGPVLLPDNH YLSTQSALSK DPNEKRDHMV LLEFVTAAGI TLGMDELYKS   240
GGMSATAATV PPAAPAGEGG PPAPPPNLTS NRRLQQTQAQ VDEVVDIMRV NVDKVLERDQ   300
KLSELDDRAD ALQAGASQFE TSAAKLKRKY WWKNLKMMII LGVICAIILI IIIVYFST    358

SEQ ID NO: 7            moltype = AA  length = 116
FEATURE                 Location/Qualifiers
source                  1..116
```

```
                                mol_type = protein
                                organism = Rattus norvegicus
SEQUENCE: 7
MSATAATVPP  AAPAGEGGPP  APPPNLTSNR  RLQQTQAQVD  EVVDIMRVNV  DKVLERDQKL    60
SELDDRADAL  QAGASQFETS  AAKLKRKYWW  KNLKMMIILG  VICAIILIII  IVYFST       116

SEQ ID NO: 8               moltype = AA   length = 116
FEATURE                    Location/Qualifiers
source                     1..116
                           mol_type = protein
                           organism = Mus musculus
SEQUENCE: 8
MSATAATVPP  AAPAGEGGPP  APPPNLTSNR  RLQQTQAQVD  EVVDIMRVNV  DKVLERDQKL    60
SELDDRADAL  QAGASQFETS  AAKLKRKYWW  KNLKMMIILG  VICAIILIII  IVYFST       116

SEQ ID NO: 9               moltype = AA   length = 116
FEATURE                    Location/Qualifiers
source                     1..116
                           mol_type = protein
                           organism = Homo sapiens
SEQUENCE: 9
MSATAATAPP  AAPAGEGGPP  APPPNLTSNR  RLQQTQAQVD  EVVDIMRVNV  DKVLERDQKL    60
SELDDRADAL  QAGASQFETS  AAKLKRKYWW  KNLKMMIILG  VICAIILIII  IVYFST       116
```

PEPTIDES FOR CHARACTERIZATION OF *botulinum* NEUROTOXINS

This application is a continuation of U.S. patent application Ser. No. 18/137,604, filed Apr. 21, 2023, which is a continuation of U.S. Pat. No. 11,661,442, filed Mar. 22, 2021, which is a continuation of U.S. Pat. No. 10,975,125, filed Dec. 12, 2019, which is a continuation of U.S. Pat. No. 10,508,135, filed Feb. 4, 2019, which is a continuation of U.S. Pat. No. 10,246,492, filed Nov. 13, 2015, which is a continuation-in-part of U.S. Pat. No. 9,453,254, filed Aug. 17, 2012, which is a US national phase application based on PCT/US2010/052847 filed Oct. 15, 2010, which claims priority to U.S. Provisional Application No. 61/252,315, filed Oct. 16, 2009.

FIELD OF THE INVENTION

The field of the invention is cell based assays for protease activity that utilize fluorescence, especially protease assays for *Botulinum* neurotoxins BoNTs that cleave synaptobrevin.

BACKGROUND OF THE INVENTION

*Botulinum* neurotoxins (BoNTs) are extremely toxic proteins and can be classified into distinct subgroups based, inter alia, on peptide sequence and/or substrate specificity. All of the naturally occurring BoNTs (BoNT/A-G) are composed of a heavy chain that mediates toxin entry into a target cell and a light chain with zinc-dependent protease activity that hydrolyzes selected SNARE proteins that mediate fusion of neurotransmitter vesicles to the membrane that forms part of the synaptic cleft.

For example, the light chain of BoNT/A hydrolyzes with high specificity SNAP-25, which is required for vesicle-mediated exocytosis of acetylcholine into the synaptic cleft. Known assays for such hydrolytic activity include those described in our copending International Application (WO 2009/035476), which is incorporated by reference herein. Here, a fluorophore and a quencher are covalently linked to the respective ends of a peptide sequence that includes, for example, the SNAP-25 sequence. Cleavage by BoNT/A (or other BoNTs with a substrate specificity towards SNAP-25) will result in physical separation of the cleavage products and so reduce fluorescence quenching, which can then be quantified. Among other choices, it is often preferred that such assay is performed as an in vitro solid-phase based assay.

While such assay is conceptually simple and can be used to readily determine BoNT/A, BoNT/C, or BoNT/E activity, such assay can not be simply modified to a cell-based assay for determination of BoNT/B, BoNT/D, BoNT/F, or BoNT/G activities by replacing the SNAP-25 motif with a SNARE domain as the SNARE domain includes a membrane spanning sub-domain that would place the N-terminal fluorophore into a vesicle lumen. In such case, only diffusion of the fluorescence signal would be observed as has been reported elsewhere (Dong et al. PNAS (2004), Vol. 101, No. 41, 14701-14706; or U.S. Pat. App. No. 2006/0134722).

Therefore, there is still a need for improved BoNT assays, and especially cell-based assays for BoNTs that cleave synaptobrevin.

SUMMARY OF THE INVENTION

The present invention is directed to various compositions and methods of analyzing BoNT protease activity, and especially BoNT/B, BoNT/G, BoNT/D, and/or BoNT/F protease activity in a cell-based system using a pair of fluorophores. The cells express two recombinant hybrid proteins, where one of the hybrid proteins includes at least one BoNT protease recognition and cleavage sequence, along with a transmembrane domain that is not cleavable by the BoNT protease and that directs the hybrid protein to an intracellular synaptic vesicle.

One aspect of the inventive subject matter is an expression vector that includes two encoding regions encoding two hybrid proteins having a structure of A-C-B and A-C'-D, respectively and further encoding N-terminal palmitoylation sequences. In these encoded hybrid proteins A is a protein domain that is not cleavable by the BoNT protease, B is a first fluorescent protein, C is a BoNT protease recognition and cleavage sequence, C' is a non-cleavable analog of a BoNT protease recognition and cleavage sequence, and D is a second fluorescent protein. In some embodiments the first and second fluorescent proteins are positioned such that when the two hybrid proteins are collocated on a cell membrane no useful FRET is produced on colocation to a cell membrane. In other embodiments the two hybrid proteins are positioned such that FRET is observed on colocation on a cell membrane. When such a transfected cell is contacted with a BoNT protease it can take up the BoNT protease, resulting in release of the first fluorescent protein.

Another aspect of the inventive subject matter is a cell that incorporates an expression vector. Such an expression vector includes two encoding regions encoding two hybrid proteins having a structure of A-C-B and A-C'-D, respectively and further encoding N-terminal palmitoylation sequences. In these encoded hybrid proteins A is a protein domain that is not cleavable by the BoNT protease, B is a first fluorescent protein, C is a BoNT protease recognition and cleavage sequence, C' is a non-cleavable analog of a BoNT protease recognition and cleavage sequence, and D is a second fluorescent protein. In some embodiments the first and second fluorescent proteins are positioned such that when the two hybrid proteins are collocated on a cell membrane no useful FRET is produced on colocation to a cell membrane. In other embodiments the two hybrid proteins are positioned such that FRET is observed on colocation on a cell membrane. When such a transfected cell is contacted with a BoNT protease it can take up the BoNT protease, resulting in release of the first fluorescent protein.

Various objects, features, aspects and advantages of the present invention will become more apparent from the following detailed description of preferred embodiments of the invention.

BRIEF DESCRIPTION OF THE DRAWING

Prior Art

FIGS. 5A and 5B schematically depict an alternative embodiment of an intermolecular assay for BoNT activity.

DETAILED DESCRIPTION

According to the present invention a cell-based FRET assay for BoNT (and especially for BoNT/B, BoNT/D, BoNT/F, or BoNT/G) is provided in which a cell is transfected cell such that the cell produces (a) a single hybrid protein having a structure of A-B-C-D, or (b) two distinct hybrid proteins having a structure of A-C-B and A-C-D, respectively, in which A is a transmembrane domain, B is a first fluorescent protein, C is BoNT protease recognition and cleavage sequence, and D is a second fluorescent protein, where most typically, B and D allow for a FRET assay.

This application incorporates the contents of the Sequence Identification listing entitled "BioMadison 06US7 SEQ ID.xml", created Jun. 18, 2024 and having a size of 27 KB, which accompanies the filing of the instant application.

It should be appreciated that the hybrid protein(s) that are formed in the so transfected cells include a transmembrane domain. Therefore, these proteins are expected to locate to intracellular vesicles and to so present a vesicle-bound substrate. Upon exposure of the cells with BoNT, heavy chain-mediated endocytosis of the BoNT into the transfected cell is followed by presentation of the light chain on the outer surface of the vesicle, allowing the protease activity of the light chain to cleave the cleavage sequence of the hybrid protein(s), thus reducing FRET and providing a quantifiable signal. Therefore, it should be appreciated that the compositions and methods presented herein allow for a cell-based assay in which uptake, processing, and proteolytic activity can be monitored under conditions that closely resemble the natural conditions.

Figure 1A:
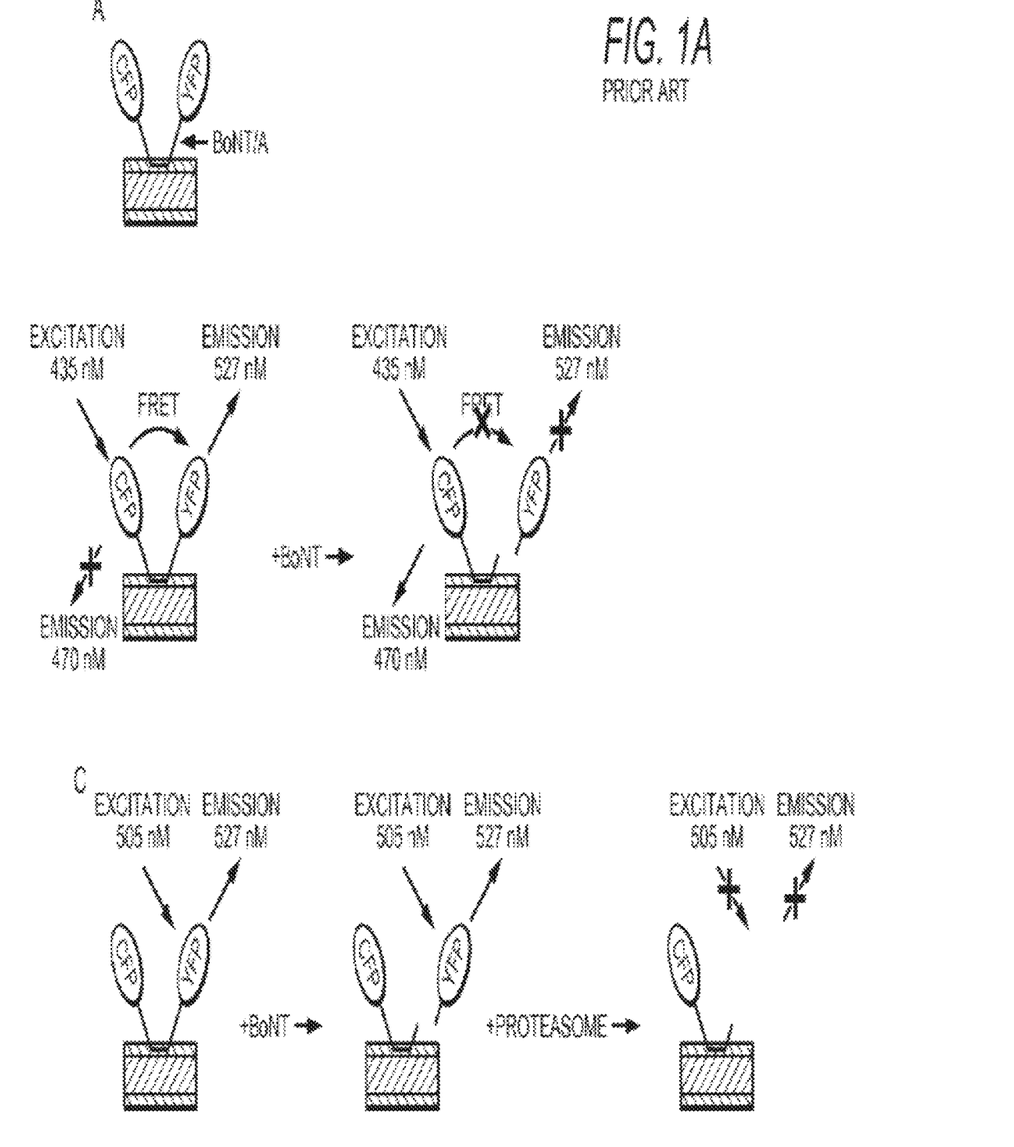
FIGS. 1A-1B are known FRET assays for BoNT protease activity in which two fluorescent proteins are separated by a SNAP25 recognition and cleavage sequence.
Figure 1B:
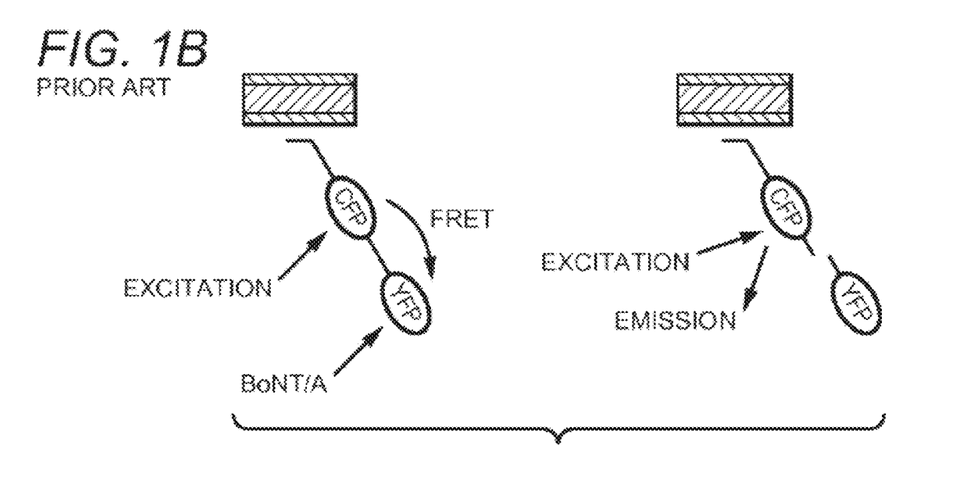

In contrast, as schematically depicted in Prior Art FIG. 1A, a BoNT/A test system with a hybrid protein is shown in A. The hybrid protein has first and second fluorescence proteins (CFP and YFP, respectively) covalently coupled to the respective termini of an intermediate peptide sequence that also includes a SNAP-25 sequence (which is the substrate for the BoNT/A light chain protease). Excitation of the CFP results in FRET-mediated fluorescence emission of YFP, thus creating a specific spectral fluorescence signature as schematically illustrated in B. Upon incubation with BoNT/A, the SNAP-25 sequence is hydrolyzed and YFP is released from the hybrid molecule (the remainder of which is still bound to a membrane or other solid phase) as depicted in C. Alternatively, or additionally, excitation and emission may be followed only using YFP, which when separated from the hybrid protein, will ultimately be processed in the proteasome complex. Similarly, as shown in Prior Art FIG. 1B, a hybrid protein has first and second fluorescence proteins (CFP and YFP, respectively) covalently coupled to the respective termini of an intermediate peptide sequence that also includes a SNAP-25 sequence. The hybrid protein is associated to the outside of the vesicle via the cysteine rich domain of the SNAP-25 sequence. Once more, upon cleavage of the SNAP-25 linker between the CFP and YFP, FRET is no longer available, and fluorescence can be measured either as loss in FRET or ultimately loss in YFP as described above.

While such systems provide various advantages, it should be readily apparent that that where the SNAP-25 sequence is replaced by a synaptobrevin (VAMP), the presence of the transmembrane sub-domain in synaptobrevin will lead to physical separation of the CFP and YFP by the vesicle (or other) membrane, thus abolishing any FRET between the CFP and YFP as is shown in FIG. 9B of U.S. Pat. App. No. 2006/0134722.

To overcome these difficulties, the inventors now have prepared hybrid molecules suitable for intramolecular FRET in which one fluorescent protein (or other reporter) is positioned between the transmembrane sub-domain and the BoNT protease recognition and cleavage sequence, and wherein another fluorescent protein (or other reporter) is positioned following the BoNT protease recognition and cleavage sequence. Additionally, the inventors have also prepared pairs of hybrid molecules suitable for intermolecular FRET in which both hybrid molecules have a respective fluorescent protein coupled to respective sequences that include a transmembrane domain and a BoNT protease recognition and cleavage sequence.

As used herein, the term "transmembrane domain" refers to any molecular moiety that is capable of insertion into a plasma membrane in a manner such that at least a portion of the moiety extends into (and more typically across) the lipid bilayer. Thus, a moiety that only externally contacts (e.g., via ionic or electrostatic interaction) the outer surface of the plasma membrane is not considered a transmembrane domain under the definition provided herein. Thus, especially preferred transmembrane domains include hydrophobic polypeptide domains that extend into (and more typically across) the plasma membrane. Most typically, preferred transmembrane domains comprise a (typically recombinant) polypeptide. However, it should be recognized that various alternative elements (e.g., N-terminal palmitoylation) will also fall within the scope of the definition provided herein.

As also used herein, the term "BoNT recognition and cleavage sequence" refers to any molecular moiety that can be bound and cleaved by a BoNT protease. It is generally preferred that the BoNT recognition and cleavage sequence comprises a synaptobrevin polypeptide or portion thereof, which is typically a recombinant polypeptide.

In one especially preferred aspect of the inventive subject matter, contemplated recombinant nucleic acids may include a sequence that encodes (I) a hybrid protein having a structure of A-B-C-D or (II) at least one of two hybrid proteins having a structure of A-C-B and having a structure of A-C-D, respectively, where A is a transmembrane domain, B is a first fluorescent protein, C is a BoNT recognition and cleavage sequence, and D is a second fluorescent protein. Most preferably, where the sequence encodes two hybrid proteins, expression of the two hybrid proteins is under the control of respective promoters (typically, but not necessarily, having the same strength and same regulatory control mechanism).

Most typically, the transmembrane domain is selected such as to allow insertion of the recombinant protein(s) into the membrane of synaptic vesicles. Therefore, it is generally preferred that the transmembrane domain is the transmembrane domain of synaptobrevin, synaptophysin, synapsin I, synapsin II, and/or synapsin III, or any portion thereof that still confers anchoring of the recombinant protein into the membrane. However, in alternative aspects of the inventive subject matter, it is contemplated that various other transmembrane domains are also deemed suitable so long as such domains will anchor the recombinant protein to one or more intracellular membranes. There are numerous transmembrane domains known in the art, and all of those are deemed suitable for use herein. The person of ordinary skill in the art will readily be able to identify a domain as a transmembrane domain (e.g., via publication and description of the domain, or via computational domain analysis). Of course, suitable domains naturally occurring domains as well as mutated forms thereof (e.g., forms with one or more transitions, transversions, insertions, deletions, inversions, etc.). Moreover, additionally contemplated transmembrane domain may also be entirely synthetic and based on computational analysis.

Similarly, it should be appreciated that the transmembrane domain may also be replaced by another polypeptide moiety that allows at least temporary anchoring of the hybrid protein to a membrane such that the remainder of the hybrid protein is exposed to the cytosol. Anchoring may be mediated by various (typically non-covalent) interactions, including ionic, hydrophobic, and/or electrostatic interactions. Still further contemplated transmembrane domains also include non-protein transmembrane domains. For example, especially preferred alternative transmembrane domains will include those in which a hydrophobic group (e.g., sterol, hydrocarbon, etc.) is attached to the protein, and particularly a palmitoyl group. Such groups may be added intracellularly (e.g., via palmitoylation signal) or in vitro using various synthetic schemes.

It should further be appreciated that suitable transmembrane domains will preferably not include a BoNT protease cleavage site and/or a BoNT protease recognition site and thus only be acting as a transmembrane anchor for the recombinant protein. Therefore, suitable transmembrane domains may include full-length (or substantially full-length) synaptobrevin that has been sufficiently mutated to eliminate the cleavage site and/or recognition site. Alternatively, the synaptobrevin (or other transmembrane domain) may be truncated such that at least the cleavage site and/or recognition site is removed. Moreover, while the above is directed to single transmembrane domains, it should be appreciated that more than one transmembrane domains are also deemed appropriate (which are preferably coupled to each other via a spacer).

With respect to first and second fluorescent proteins it is generally contemplated that all known fluorescent proteins are suitable for use herein so long as such proteins can be used as specific and distinct signal generation moieties. However, it is particularly preferred that the signal generation moieties are fluorescent proteins that are suitable for FRET. For example, first and second fluorescent proteins can be Cyan Fluorescent Protein (CFP) and Yellow Fluorescent Protein (YFP) and their respective modifications, respectively. Of course, and as already noted above, the fluorescent proteins may be modified to include one or more specific characteristics (e.g., spectral) or be truncated to a specific size. Among other choices, contemplated fluorescent proteins include various blue fluorescent proteins (e.g., EBFP, EBFP2, Azurite, mKalama1), various cyan fluorescent proteins (e.g., ECFP, Cerulean, CyPet), various green fluorescent proteins (e.g., AcGFP1, ZsGreen1), and various yellow fluorescent protein derivatives (e.g., YFP, Citrine, Venus, YPet).

Similarly, it should be appreciated that the BoNT protease recognition and cleavage sequence may vary considerably, so long as such sequence is still recognized and hydrolyzed by a BoNT light chain. For example, the BoNT protease recognition and cleavage sequence may be of human, rat, or murine origin, may be present in oligo-multimeric form, and may be further specifically modified to facilitate or at least partially inhibit cleavage. Alternatively, the BoNT protease recognition and cleavage sequence may also be modified to allow identification of one or more specific BoNT subtypes (e.g., BoNT/B, D, F, and/or G, as well tetanus toxin) by preferential or exclusive cleavage. Of course, it should be recognized that all isoforms and mutants of BoNT protease recognition and cleavage sequences are also deemed suitable for use in conjunction with the teachings presented herein so long as such forms and mutants are also cleavable by one or more BoNT proteases. For example, suitable protease recognition and cleavage sequences include those from VAMP (Synaptobrevin) 1, 2, 3, 4, 5, 6, 7, or 8, and exemplary sequences are listed below where the recognition and cleavage domain is in regular type font, the transmembrane domain is in cursive type font, and where the actual cleavage positions for the respective BoNT proteases are underlined (QK: BoNT/F; KL: BoNT/D; QF: BoNT/B and TeTN; AA: BoNT/G):

Rat Vamp2 Protein sequence (SEQ ID NO: 7):
SEQ ID NO: 7
MSATAATVPPAAPAGEGGPPAPPPNLTSNRRLQQTQAQVDEVVDIMRVNV

DKVLERDQKLSELDDRADALQAGASQFETSAAKLKRKY*WWKNLKMMIILG*

*VICAIILIIIIVYFST*

Mouse Vamp2 Protein sequence (SEQ ID NO: 8):
(SEQ ID NO: 8)
MSATAATVPPAAPAGEGGPPAPPPNLTSNRRLQQTQAQVDEVVDIMRVNV

DKVLERDQKLSELDDRADALQAGASQFETSAAKLKRKY*WWKNLKMMIILG*

*VICAIILIIIIVYFST*

Human Vamp2 Protein sequence (SEQ ID NO: 9):
(SEQ ID NO: 9)
MSATAATAPPAAPAGEGGPPAPPPNLTSNRRLQQTQAQVDEVVDIMRVNV

DKVLERDQKLSELDDRADALQAGASQFETSAAKLKRKY*WWKNLKMMIILG*

*VICAIILIIIIVYFST*

Of course, it should be noted that the above sequences merely serve as examples for the sequences from which the transmembrane domain and the BoNT protease recognition and cleavage sequences can be obtained from. Thus, it is also noted that numerous alternative sequences other than synaptobrevin are also contemplated particularly if they can be cleaved by a naturally occurring or a synthetic or designer BoNT, including SNAP-25 and mutant forms thereof.

It should further be appreciated that one or more of the transmembrane domain, the first and second fluorescent proteins, and the BoNT protease recognition and cleavage domain may be truncated while retaining the respective function (i.e., transmembrane anchor, fluorescence, BoNT protease recognition and cleavage). Moreover, it should be appreciated that one or more amino acids in the above elements may be deleted or replaced by one or more other amino acids, typically in a conserved fashion.

Moreover, it is especially contemplated that the additional amino acids may be added as spacers between one or more of the transmembrane domain, the first and second fluorescent proteins, and the BoNT protease recognition and cleavage domain. Such spacers may be included to provide further steric flexibility, increase distance between the elements, etc. Typically, suitable spacers will have a length of between 1-100 amino acids, more typically between 2-50 amino acids, and most typically between 3-12 amino acids. Where the recombinant protein is used for FRET assays, shorter spacers are generally preferred. Still further, it is noted that additional domains may be provided to impart further desired functions. For example, suitable additional domains will include affinity tags for case of isolation or antibody-based labeling, cell trafficking to direct the recombinant protein into a desired compartment, etc.

Figure 3A:
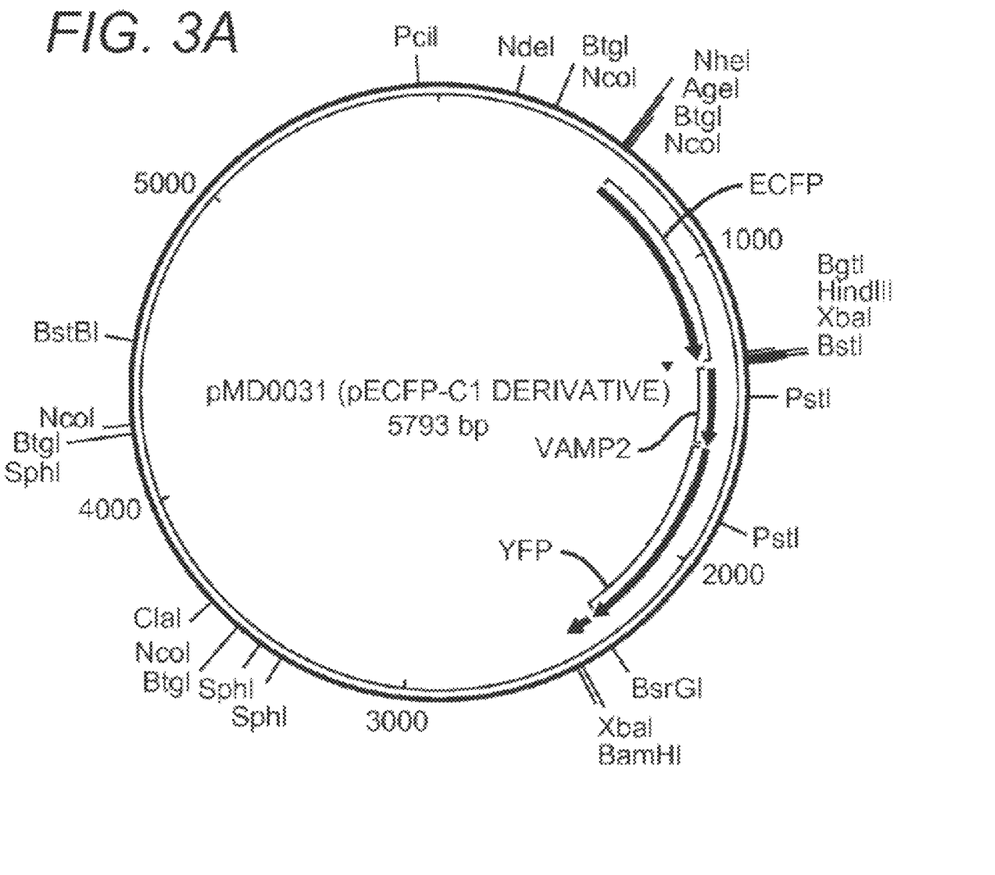
FIGS. 3A-3B are exemplary vector maps for recombinant intramolecular (3A) and intermolecular (3B) FRET constructs according to the inventive subject matter.
Figure 3B:
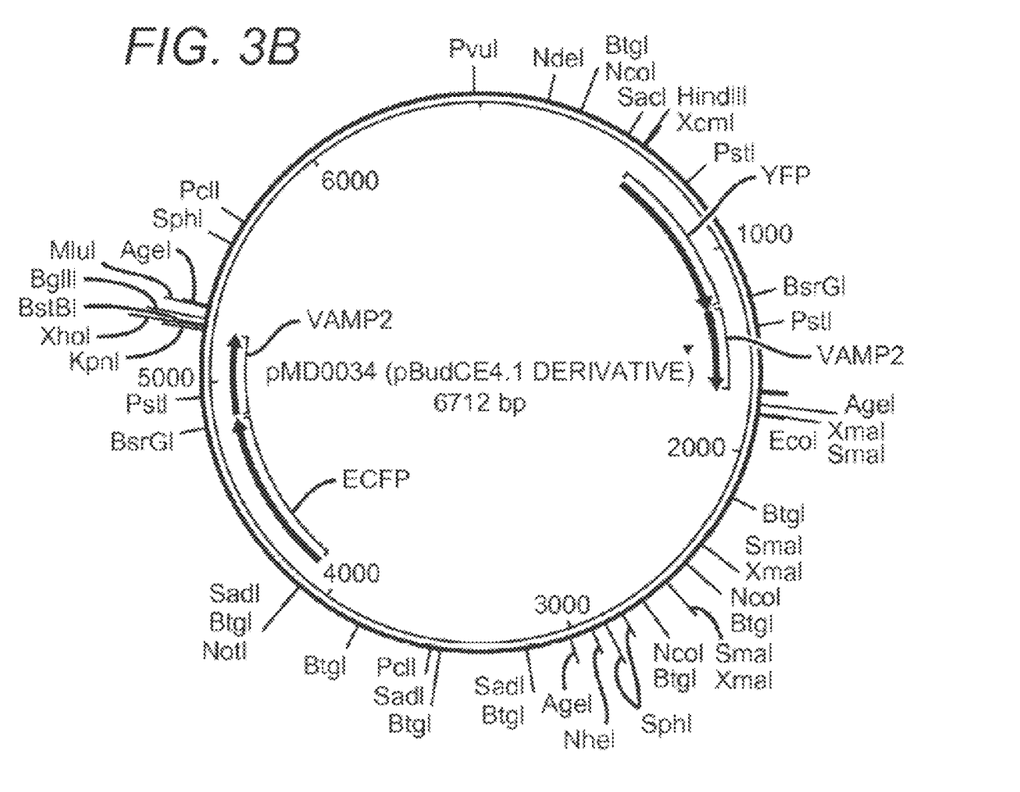

With respect to the transfected cells expressing the hybrid protein it is generally preferred that the cell is stably transfected. Nevertheless, transient transfection is also contemplated. There are numerous promoter structures known in the art, and all of those are generally deemed suitable for use herein. However, it is especially preferred that the expression is inducible from the promoter. In further contemplated aspects, expression may also be constitutively. FIG. 3A depicts an exemplary vector map for an expression construct of a hybrid protein having a structure of A-B-C-D, and FIG. 3B depicts an exemplary vector map for expression of two hybrid proteins having a structure of A-C-B and A-C-D, respectively.

Particularly preferred cells for transfection include neuronal cells (e.g., astrocytes, dendrocytes, glia cells, etc.) and stem cells (e.g., adult pluripotent, or adult germ line layer, or adult progenitor). However, numerous other non-neuronal cells, including human, rodent, insect cells, and even yeast and bacterial cells are also contemplated herein.

Consequently, the inventors contemplate a cell-based method of measuring protease activity of a BoNT protease in which in one step a transfected cell is provided that produces (I) a hybrid protein having a structure of A-B-C-D or (II) two hybrid proteins having a structure of A-C-B and A-C-D, respectively, wherein A is a transmembrane domain, B is a first fluorescent protein, C is a BoNT recognition and cleavage sequence, and D is a second fluorescent protein. In exemplary aspects of the inventive subject matter, the hybrid protein having a structure of A-B-C-D has a sequence according to SEQ ID NO:2, which is preferably encoded by a nucleic acid having sequence according to SEQ ID NO:1. Where the hybrid proteins have a structure of A-C-B and A-C-D, the protein sequences will preferably be as shown in SEQ ID NO:4 and SEQ ID NO:6, which are preferably encoded by a nucleic acid having sequence according to SEQ ID NO:3 and SEQ ID NO:5, respectively. Of course, and as already noted earlier, all mutant forms of the above sequences are also expressly contemplated herein, so long as such mutant forms retain the respective functions as noted above. In another step, the transfected cell is contacted with a BoNT protease under conditions to allow the cell to take up the BoNT protease, and in yet another step, fluorescence is measured from at least one of the first and second fluorescent proteins in the transfected cell.

Figure 2A:
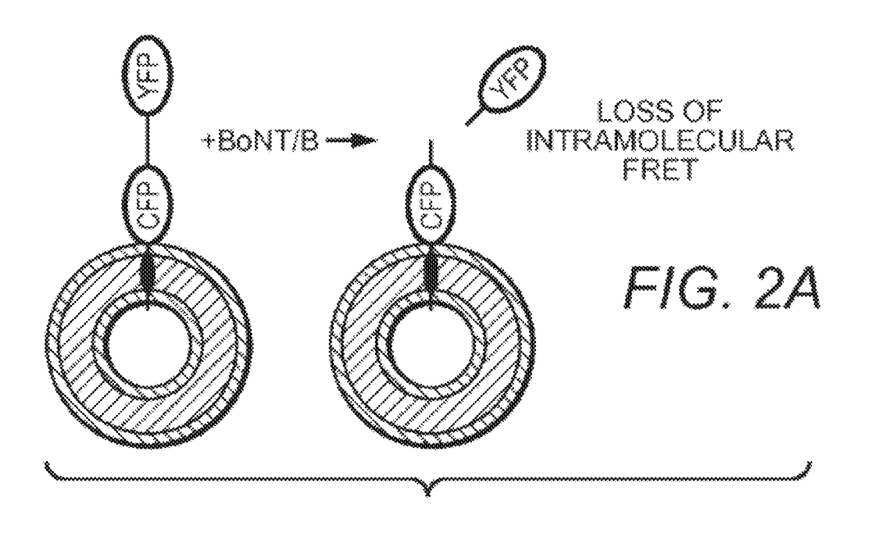
FIGS. 2A-2B are schematic illustrations for intramolecular (2A) and intermolecular (2B) FRET assays for BoNT protease activity according to the inventive subject matter.

Depending on the particular requirements and conditions, contemplated cell based assays may be performed as depicted in FIG. 2A in which the hybrid protein is a single polypeptide chain having an N-terminal transmembrane domain, followed by a CFP, which is in turn followed by a BoNT protease recognition and cleavage sequence, which is in turn followed by a (preferably terminal) YFP. Expression of the hybrid protein and subsequent translocation of the hybrid protein to the membrane of an intracellular vesicle will result in the presentation of the hybrid protein on the outside of the vesicle. The protease activity of BoNT/B will then intracellularly cleave the cleavage sequence, thus releasing the YFP from the hybrid protein. Consequently, quenching is reduced and fluorescence of the YFP is detectable in diffused form from the cell.

Figure 2B:
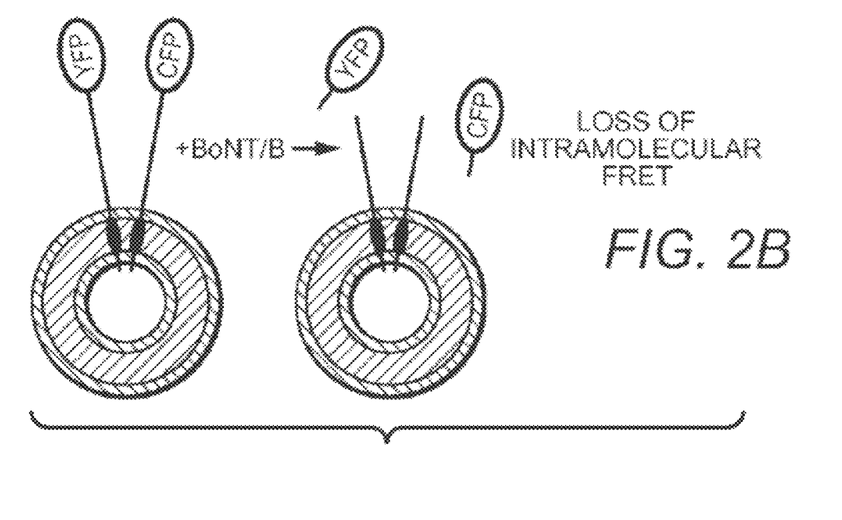

Alternatively, as shown in FIG. 2B, two separate hybrid proteins are formed in the cell, each having an N-terminal transmembrane domain, followed by a BoNT protease recognition and cleavage sequence, which is in turn followed by a (preferably terminal) YFP and CFP, respectively. Expression of the hybrid proteins and subsequent translocation of the hybrid proteins to the membrane of an intracellular vesicle will result in the presentation of the hybrid proteins on the outside of the vesicle. The protease activity of BoNT/B will then intracellularly cleave the cleavage sequences, thus releasing YFP and CFP from the hybrid protein. Consequently, quenching is reduced and fluorescence of the YFP and CFP is detectable in diffused form from the cell. Remarkably, the respective hybrid proteins co-locate on the vesicular membrane in such a manner as to allow for FRET. Exemplary results for such assays are depicted in the calculated fluorescence microphotographs of FIG. 4A and the corresponding bar graph representations of FIG. 4B. As can be readily taken from these figures, the FRET assay performed well in the intermolecular FRET assay and less satisfactorily in the intramolecular FRET assay. However, it is expected that routine experimentation will also provide satisfactory intramolecular FRET assay results.

In other embodiments, two separate hybrid proteins are formed in the cell, each having an N-terminal transmembrane domain. One of the hybrid proteins includes a fluorophore (for example, a peptide fluorophore derived from Green Fluorescent Protein) and a BoNT protease recognition sequence and cleavage sequence that intervenes between and is joined to both the transmembrane domain and the fluorophore. The second hybrid protein includes a second, different fluorophore (for example, a different peptide fluorophore derived from Green Fluorescent Protein) and a second, distinct non-cleavable intervening peptide sequence that does not include a BoNT cleavage sequence and is joined to both the transmembrane domain and the fluorophore. In some embodiments the second intervening peptide sequence can include a BoNT protease recognition sequence or a portion of a BoNT substrate protein, but does not include a BoNT cleavage sequence. In such a second hybrid protein the BoNT cleavage sequence can be partially or completely excised, modified by substitution with non-native amino acids, or be modified by post-translational modification (for example, treatment with reagents reactive with amino acid side chains). Peptide sequences associated with recognition by BoNTs and the sequences associated with cleavage by BoNTs can be found in the literature, for example in Sikorra et al., "Substrate Recognition Mechanism of VAMP/Synaptobrevin-cleaving Clostridial Neurotoxins" J. Biol. Chem. 283(30):21145-21152 (2008).

In such an embodiment the two hybrid proteins can associate and form all or part of a reporting construct complex. On exposure to a BoNT having specificity for the cleavage site sequence (for example, exposure of a synaptobrevin-based reporting construct complex to BoNT/B), only the fluorophore associated with the cleavage site-containing intervening sequence is released, whereas the fluorophore associated with the intervening sequence that does not include such a cleavage site is retained at the membrane. In preferred embodiments, the fluorophore associated with the cleavage site-containing intervening sequence is selected to be degradable by components of the cytosol, and release by a BoNT results in degradation of the released fluorophore relative to fluorophore associated with the membrane. In some embodiments, such a releasable fluorophore is selected to be more rapidly degraded (for example 1.5, 3, 10, 30, 100, or more than 100 times faster) in the cytosol than the fluorophore associated with the non-cleavable intervening sequence if found in the cytosol. For example, YFP can be associated with the cleavage site-containing intervening sequence and CFP can be associated with the intervening sequence that lacks a BoNT susceptible cleavage site. In some embodiments the fluorophores can be selected, oriented, and/or spaced such that meaningful (i.e. >5%) Foerster resonance energy transfer occurs between donor and acceptor fluorophore. In other embodiments, the fluorophores can be selected, oriented, and/or spaced such that no meaningful (i.e. less than or equal to 5%) Foerster resonance energy transfer occurs between the fluorophores.

In such embodiments, the fluorophore associated with the intervening sequence that lacks a BoNT cleavage sequence remains associated with a membrane following exposure to a BoNT. The emission from such a fluorophore can be utilized to normalize the emission observed from the fluorophore that is associated with the intervening sequence that includes a BoNT cleavage site, for example by calculating a ratio. Such normalization can be used to reduce assay variation resulting from differences in cell density, size, and/or distribution between different wells of test plate in a cell-based assay for BoNT activity.

FIGS. 5A and 5B depict an embodiment of the inventive concept in which two hybrid proteins, one of which is not cleaved by a BoNT, are utilized. FIG. 5A shows a membrane 510 (for example, a vesicle membrane) that includes a reporting construct complex 520 prior to the introduction of or in the absence of a BoNT. The reporting construct complex includes at least two peptides. One peptide includes a first fluorophore 550 that is coupled to a transmembrane portion 565 by an intervening peptide 560. The intervening peptide 560 includes BoNT recognition and BoNT cleavage sequences, and hence is susceptible to cleavage by the proteolytic activity of a BoNT having specificity for those recognition and cleavage sequences. The other peptide includes a second fluorophore 530 that is coupled to a transmembrane portion 545 by an intervening peptide 540. The intervening peptide 540 is not cleavable by the BoNT that is capable of cleaving intervening peptide 560. In some embodiments the intervening peptide 540 is an analog of intervening peptide 560 (i.e. having 50%, 60%, 70%, 80%, 90%, 95%, or greater than 95% sequence identity) that does not include the BoNT cleavage site. For example, the intervening peptide 560 can include a synaptobrevin sequence than includes BoNT/B recognition and BoNT/B cleavage sequences, whereas intervening peptide 540 can include a synaptobrevin sequence that retains BoNT/B recognition sequences and does not include the BoNT/B cleavage sequence. The fluorophores 530 and 550 are distinguishable from one another (for example, by having different excitation/emission spectra), and can be selected and positioned (i.e. via spacing and/or orientation) to form a FRET pair, for example by selecting fluorophore 530 to have an emission spectrum that overlaps the excitation spectrum of fluorophore 550. In other embodiments the fluorophores can be selected and/or positioned such that significant FRET (i.e. >5%) does not occur.

FIG. 5B depicts the result of exposure of the reporting construct complex of FIG. 5A to a BoNT capable of cleaving the intervening peptide 560. As shown, such cleavage results in the cleavage of the intervening peptide into two fragments, 560A and 560B. Fragment 560B remains with the transmembrane sequence 565 while fragment 560 remains with the associated fluorophore 550, which is released into the cytoplasm. Since intervening peptide 540 is not cleaved, fluorophore 530 remains attached to the membrane following exposure to the BoNT. Release of fluorophore 550 can (in the case of reporting construct complexes exhibiting FRET) result in loss of FRET that is detectable by loss of emissions from the fluorophore. In addition, release into the cytosol can result in degradation of fluorophore 550, which can be detected by loss of emission from the fluorophore. Fluorophore 530, however, is not subject to cytosolic degradation, and as a result emission continues following BoNT treatment. In some embodiments an emission measurement from the fluorophore retained on the membrane following BoNT exposure is used to correct for variations in cell density, size, and/or distribution between wells of a test plate. This can be accomplished, for example, by calculating a ratio between the fluorescence emission measured from the fluorophore released by BoNT treatment and the fluorescence emission measured from the fluorophore retained following BoNT treatment.

EXAMPLES

Cloning of Intramolecular Construct

The intramolecular FRET construct, pMD0031 (FIG. 3A), was constructed in pEGFP-C1 (Clontech, Mountain View, CA). Three DNA fragments- an N-terminal fragment of rat Vamp2 from the start to amino acid 92, full length YFP without a stop codon, and a C-terminal fragment of rat Vamp2 from amino acid 93 to the stop-were amplified by polymerase chain reaction (PCR). An EcoRI restriction site was engineered onto the 5' end of the N-terminal Vamp2 fragment and a SerGlyGly (TCGGGAGGC) linker and the first 12 nucleotides of the YFP were engineered onto the 3' end. The YFP fragment had the last 13 nucleotides of the N-terminal Vamp2 fragment and the same SerGlyGly linker as the N-terminal Vamp2 fragment engineered onto the 5' end and a second SerGlyGly (AGCGGCGGT) linker and the first 9 nucleotides of the C-terminal Vamp2 fragment engineered onto the 3' end. The C-terminal Vamp2 fragment had the last 12 nucleotides of YFP without a stop and the same SerGlyGly linker as the YFP fragment engineered onto the 5' end and a BamHI restriction site engineered onto the 3' end.

These three fragments were then combined using splice overlap extension (SOE) PCR to create a single fragment consisting of an EcoRI restriction site, the N-terminal fragment of rat Vamp2 (amino acids 1-92), a SerGlyGly linker, YFP without a stop, a second SerGlyGly linker, the C-terminal fragment of rat Vamp2 (amino acids 93-stop), and an BamHI restriction site. This fragment and pECFP-C1 were then digested with EcoRI and BamHI, ligated together, and transformed into DH5α *E. coli*. The final construct insert was then fully sequenced.

Cloning of Intermolecular Construct

The intermolecular FRET construct, pMD0034 (FIG. 3B), was constructed in pBudCE4.1 (Invitrogen, Carlsbad, CA). The YFP rat Vamp2 fusion was generated by amplifying two fragments by PCR. The first fragment was YFP without a stop with an engineered HindIII restriction site on the 5' end and a SerGlyGly linker (AGTGGAGGC) and the first 9 nucleotides of rat Vamp2 engineered on the 3' end. The second fragment was full length rat Vamp2 with the last 9 nucleotides of YFP and the same SerGlyGly linker engineered onto the 5' end and an XbaI restriction site engineered onto the 3' end. These two fragments were then combined using SOE PCR to create a YFP, SerGlyGly linker, full length Vamp2 fragment. The fragment and pBudCE4.1 were then digested with HindIII and XbaI, ligated together, and transformed into DH5α *E. coli*. The CFP rat Vamp2 fusion was created similarly but contained a CFP without a stop, a NotI restriction site on the 5' end, and a KpnI site on the 3' end. The final construct was then fully sequenced.

Cell Culture and FRET Assay Analysis of FRET efficiency, YFP/CFP fluorescence ratios, and BoNT/B sensitivities of the BoNT/B reporters was performed in cells in vitro. More specifically, Neuro2A cells were grown in a 96-well plate to 70% confluency (~2000 cells/well) and transiently transfected using Lipofectamine 2000 (Invitrogen), with the intra- or intermolecular BoNT/B reporters. After 24 h, cells were incubated in the presence or absence of 25 nM BoNT/B at 37° C. for 72 h in 100 μl of phenol red-free MEM medium.

Figure 4A:
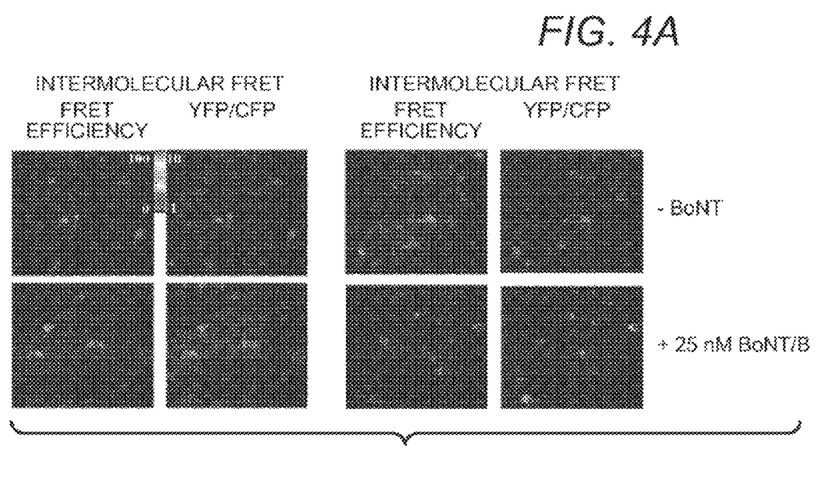
FIG. 4A depicts exemplary FRET results for intramolecular (left panel) and intermolecular (right panel) FRET analysis according to the inventive subject matter.
Figure 4B:
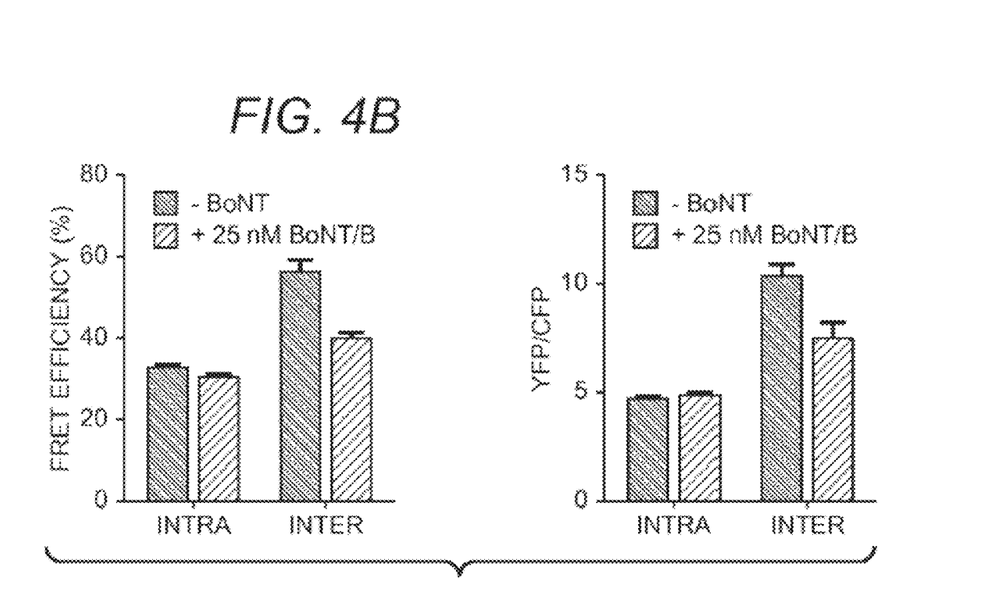
FIG. 4B is a graphic representation of the results from the experiments of FIG. 4A.
Figure 5A:
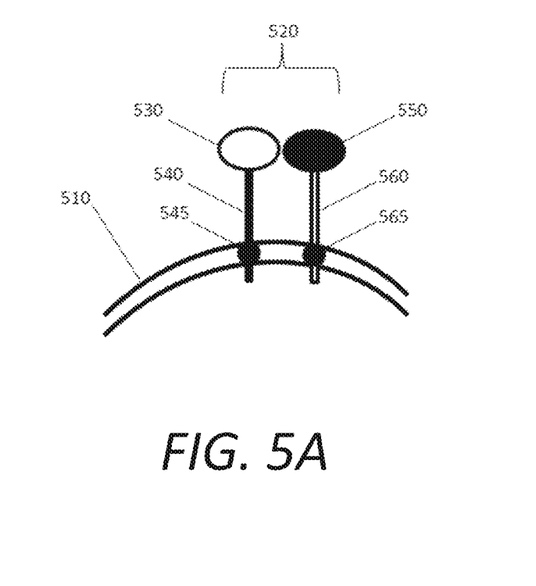
FIG. 5A depicts the assay components prior to exposure to the BoNT.
Figure 5B:
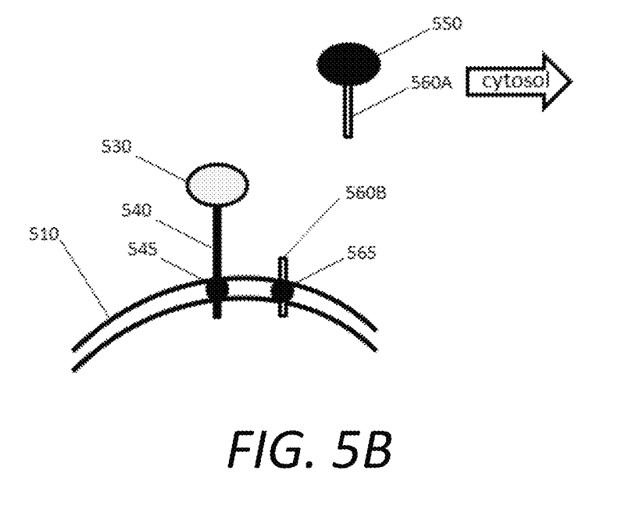
FIG. 5B depicts the assay components following exposure to the BoNT.

Semi-automated FRET or total YFP and CFP fluorescence measurements were performed using a Nikon TE2000-U fluorescent microscope with 200× magnification and Nikon NIS Elements 3.4 software. For FRET measurements, coefficients -A and -B (acceptor and donor) were calculated at 0.03 and 0.73 respectively, using a specific bleed-through method. FIG. 4A depicts randomly selected fields pseudo-colored for FRET efficiency or the YFP/CFP fluorescence ratio. YFP/CFP ratios were calculated from emissions collected upon direct excitement of each fluorophore. As can be seen from the graphic representation in FIG. 4B, the intermolecular BoNT/B reporter approach was significantly more sensitive for detection of BoNT/B in living cells. 30 randomly selected cells per condition were analyzed for FRET efficiency (FIG. 4A, left panels) or YFP/CFP fluorescence ratios (FIG. 4A, right panels) in the presence or absence of 25 nM BoNT/B. Indeed, such results were entirely unexpected as effective intermolecular FRET not only required balanced expression of the two fluorescent proteins, but also co-location of the recombinant proteins in corresponding quantities. The average signal from the 30 cells from 5 microscopic fields on 3 different wells is shown. Cells exhibiting over-saturated fluorescence were excluded.

Thus, specific embodiments and applications of BoNT assays have been disclosed. It should be apparent, however, to those skilled in the art that many more modifications besides those already described are possible without departing from the inventive concepts herein. The inventive subject matter, therefore, is not to be restricted except in the spirit of the appended claims.

What is claimed is:

1. A nucleic acid encoding a reporting construct system for measuring protease activity of a *Botulinum* neurotoxin (BoNT) protease, comprising:
   a first portion encoding a first hybrid protein having a structure of A-C-B and a second portion encoding a hybrid protein having a structure of A-C'-D;
   wherein A is an N-terminal palmytoilation sequence of the first and second hybrid proteins, B is a first fluorescent protein, C is a first linking region comprising a *Botulinum* neurotoxin protease recognition sequence and a *Botulinum* neurotoxin protease cleavage sequence, C' is a second linking region comprising an analog of C that includes the *Botulinum* neurotoxin protease recognition sequence but not the *Botulinum* neurotoxin protease cleavage sequence, B is a first fluorescent protein and D is a second fluorescent protein.

2. The nucleic acid of claim 1, wherein, in the first and second hybrid proteins provided by expression of the nucleic acid, the first fluorescent protein and the second fluorescent protein are selected, oriented, or spaced in the first and second hybrid proteins are such that less than 5% FRET occurs between the first fluorescent protein and the second fluorescent protein when the first hybrid protein and the second hybrid protein are collocated on a cellular membrane.

3. The nucleic acid of claim 1, wherein, in the first and second hybrid proteins provided by expression of the nucleic acid, the first fluorescent protein and the second fluorescent protein are selected, oriented, or spaced in the first and second hybrid proteins are such that meaningful FRET occurs between the first fluorescent protein and the second fluorescent protein when the first hybrid protein and the second hybrid protein are collocated on a cellular membrane.

4. The nucleic acid of claim 1, wherein C comprises at least two of a BoNT/B, a BoNT/G, a BoNT/D, and a BoNT/F protease recognition and cleavage sequence.

5. The reporting construct system of claim 1, wherein C comprises a portion of synaptobrevin.

6. The reporting construct of claim 1, wherein at least one of the first fluorescent protein and the second fluorescent protein is a Green Fluorescent Protein (GFP) mutation.

7. The reporting construct of claim 6, wherein the first fluorescent protein is Yellow Fluorescent Protein (YFP).

8. The reporting construct of claim 6, wherein the second fluorescent protein is Cyan Fluorescent Protein (CFP).

9. A cell comprising the nucleic acid of claim 1.

* * * * *